United States Patent [19]
Batard et al.

[11] Patent Number: 4,559,933
[45] Date of Patent: Dec. 24, 1985

[54] ORTHOPAEDIC LUMBO-SACRAL CORSET WITH SEMI-RIGID ELEMENTS AND INFLATABLE PADS

[75] Inventors: Denis Batard, Nantes; Jean-Claude Freland; Bernard Wallez, both of Basse-Goulaine; Jean Paul Desffains, Orvault; Roger Valle, Saint Herblain, all of France

[73] Assignee: S.A. Arlux, Orvault, France

[21] Appl. No.: 507,065

[22] Filed: Jun. 23, 1983

[30] Foreign Application Priority Data

Jul. 1, 1982 [FR] France .................... 82 11555

[51] Int. Cl.$^4$ ............................. A61F 5/02
[52] U.S. Cl. .................... 128/78; 128/DIG. 20; 128/88
[58] Field of Search ............ 128/DIG. 20, 78, 88, 128/89 R, 90

[56] References Cited

U.S. PATENT DOCUMENTS

| | | | |
|---|---|---|---|
| 684,411 | 10/1901 | Cook | 128/89 R |
| 2,858,827 | 11/1958 | Vilpou | 128/78 |
| 2,900,984 | 8/1959 | Cunningham | 128/78 |
| 3,071,133 | 1/1963 | Eisen | 128/78 |
| 3,680,548 | 8/1972 | Brown | 128/90 |
| 3,871,367 | 3/1975 | Miller | 128/78 |
| 4,135,503 | 1/1979 | Romano | 128/78 |
| 4,202,327 | 5/1980 | Glancy | 128/78 |

FOREIGN PATENT DOCUMENTS 2355494 10/1978 France .
2290884 8/1980 France .
2086712 5/1982 United Kingdom .

*Primary Examiner*—Gene Mancene
*Assistant Examiner*—C. W. Shedd
*Attorney, Agent, or Firm*—Young & Thompson

[57] ABSTRACT

The present invention relates to an orthopaedic lumbo-sacral corset obtained by the assembly of semi-rigid elements and of an inflatable pad. The orthopaedic lumbo-sacral corset according to the invention is made of two side half-shells of a semi-rigid plastic material, connected along the adjacent dorsal edges by a semi-rigid thin band forming a hinge adapted to be generally aligned with the spine of the wearer so as more clearly to orient the shells, with attachment and tightening structure between the adjacent front edges of the two half-shells and an inflatable lumbar pad forming two symmetrical pads relative to the axis. This orthopaedic lumbo-sacral corset is usable for the treatment of chronical lumbar diseases and difficult sciaticas.

8 Claims, 4 Drawing Figures

ORTHOPAEDIC LUMBO-SACRAL CORSET WITH SEMI-RIGID ELEMENTS AND INFLATABLE PADS

The present invention relates to orthopaedic corsets, so-called lumbo-sacral corsets, used for the preventive and corrective treatment of orthopaedic and rheumatologic lumbar diseases.

STATEMENT OF PRIOR ART

In French Pat. No. 2,290,884 corresponding to U.S. Pat. No. 3,871,367 has already been proposed to prefabricate the orthopaedic corsets of this type by providing a number of symmetrical molds of different sizes formed of an outer layer of a hard and almost rigid plastic material and an inner layer of a compressible plastic material, the shell being split along its rear axial line with releasable fixation means attached onto the adjacent posterior portions.

This type of orthopaedic lumbo-sacral corset necessitates a high number of mold sizes due to their small adaptability to the user's corpulency, is difficult to put in place and to tighten by the user himself because of the dorsal position of the releasable fixation means, and finally is little efficient for providing a self-elongation of the rachis. Moreover, said orthopaedic lumbo-sacral corset has lumbar pads of fixed volumes.

In French Pat. No. 2,355,494 has also been proposed to provide such corsets as a jacket of an inextensible or non-stretching fabric which is wrapped around the trunk and has setting means for the adjustment to the body, said jackets comprising stiffening inflatable structures one of which is fixed on the back and the other on the front in the axis of the jacket, with an inflatable abdominal pocket placed against be abdominal cavity.

Such a type of corset exhibits an insufficient rigidity and does not provide a distinctly marked sub-costal support useful for the self-elongation of the rachis.

BRIEF DESCRIPTION OF THE INVENTION

The object of the present invention is to provide an orthopaedic lumbo-sacral corset of the type formed of a plastic material shell which is adaptable to a widened range of corpulencies, benefits from the inherent rigidity of such a type of shell, whose adjustment and tightening setting on the patient are easily settable by the patient himself, has a shape which provides an increase of the intra-abdominal pressure and an elongation of the rachis, and has lumbar pads of settable volume.

A further object of the present invention is to provide an orthopaedic lumbo-sacral corset which is resistent, aesthetic, easy to use and to keep in good condition, and of a light weight.

According to the invention, these objects are fulfilled due to the fact that the orthopaedic lumbo-sacral corset is formed of two side half-shells made of a semi-rigid plastic material, connected along the adjacent dorsal edges by a semi-rigid thin band forming a hinge adapted to be generally aligned with the spine of the wearer, with attachment and tightening means between the adjacent front edges of the two half shelves and an inflatable lumbar pad forming two pads symmetrical relative to the axis.

According to a further feature of the invention, the thin flexible band which forms a hinge is applied on the rear outer surface of the two half-shells the edges of which are spread apart over some distance so as to form a space for the spinous processes. The flexible band is fixedly attached to the half-shells by riveting, glueing or any other fixation means providing a sufficient shearing strength. The use or a removable fixation means, for example by using fabric bands with small loops and hooks sold under the trade-mark of "VELCRO" allows a subsequent setting and a possible re-use.

According to another feature, the inflatable lumbar pad has a violin shape with an enlarged lower lobe. According to a preferential embodiment, the lumbar pad is subdivided into cavities or channels in the direction generally aligned in the spine of the wearer, the cross-section of which decreases from the axial line to the peripheral areas. Preferably, the lumbar pad is associated with a rigid bar, especially metallic, disposed on its face turned toward the inside and is fixedly attached to the semi-rigid thin band forming a hinge opposite the space provided for the spinous processes. This fixation can be provided by riveting the ends of the rigid blade on the flexible band.

The inflation valve can be disposed at any point, for example at the lower portion of the inflatable pad.

According to another feature, the half-shells are formed with side openings of elliptical contour at the bottom and front edges, and thereby adapted to conform to the iliac crests of the wearer. These openings enhance the adaptation of the half-shells and the setting of the waist clamp at the trochanteric level.

The general shape of the half-shells is characterized by a concave waist portion being engaged between the iliac crest and the side sub-costal area, while respecting the epigastric area, and by a concave abdominal anterior surface.

According to a preferred embodiment, the attachment and tightening means between the adjacent front edges of the two half-shells are formed of straps attached in the vicinity of the anterior edge of one of the half-shells, by rings or similar strap return members, attached in the vicinity of the anterior edge of the other half-shell and by fixation means of the ends of the straps arranged in the vicinity of the anterior edge of the first half-shell. The fixation means are preferably of the type which provides a settable tightening and, for example, of the "VELCRO" type or of the pinching buckle type. The return means for the straps can be formed of rectangular buckles rotatably mounted about their fixation point in order to accomodate a small difference of level between the two half-shells, but it is also possible, for reducing the protrusions on the anterior surface, to form them as openings with reinforced edges, provided in the surface of the half-shell.

BRIEF DESCRIPTION OF THE DRAWINGS

An embodiment of the orthopaedic lumbo-sacral corset according to the invention will be described hereafter, with reference to the accompanying drawing wherein.

PREFERRED EMBODIMENT

Figure 1:
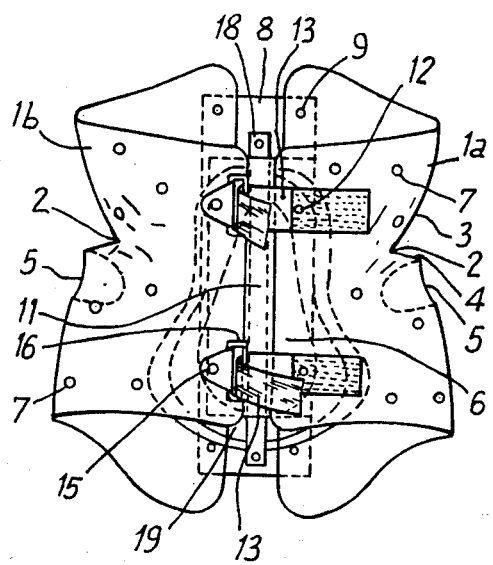
FIG. 1 is a front elevation view of the orthopaedic lumbo-sacral corset.
Figure 2:
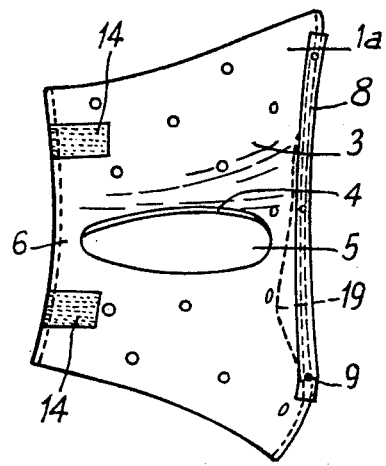
FIG. 2 is a side elevation view of the same.
Figure 3:
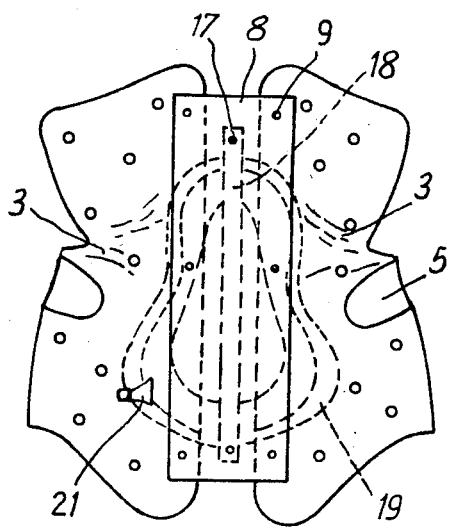
FIG. 3 is a rear view thereof.
Figure 4:
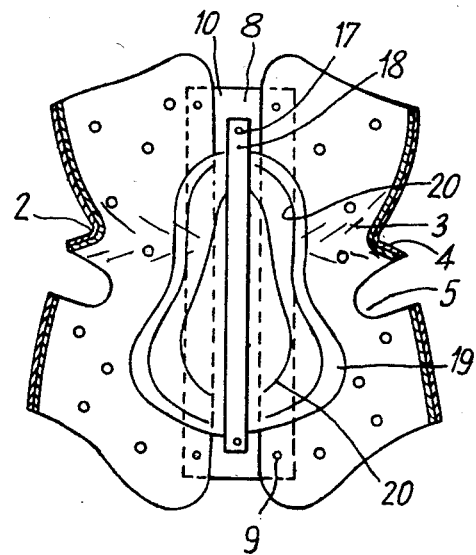
FIG. 4 is a sectional view in a vertical front plane.

The orthopaedic lumbo-sacral corset comprises two half-shells 1a and 1b having a concave area forming a waist clamp 2 which separates a sub-costal support 3 from a support area 4 on the iliac crest. Below area 4 is formed a wide opening 5 having a substantially elliptical shape in order to free the iliac crest. The front portion 6 is concave for providing an intra-abdominal pressure. As shown in FIG. 4, said half-shells are preferably made of two layers, an outer layer of a rigid thermoplastic material and an inner layer of foam, fabric or similar. Perforations 7 which can be replaced by openings of larger section ensure the ventilation.

Said half-shells are fabricated in a reduced number of sizes corresponding to all corpulencies. The setting by the fitter is possible since the two half-shells 1a and 1b are fixedly connected by a band of semi-rigid thin plastic material 8 which is attached to the two half-shells, for example by rivets 9 or by glueing, the two half-shells 1 forming between their rear edges a gutter 10 having a width of at least two centimetres for avoiding to rest directly onto the spinous processes.

In front is fixed a flexible and thin plastic material blade 11 on the neighbouring inner face of the edge of one of the half-shells 1a for example by rivets 12, which is engaged behind the half-shell 1b when the orthopaedic lumbo-sacral corset is put on. On the frontal face of half-shell 1a are fixed two straps 13 the surface of which comprises a "VELCRO" element 14. On the other half-shell 1b are fixed by means of rivets 15 rectangular buckles 16 in which the straps 13 can be engaged and which, after being tightened, are fixed by application of the VELCRO surface provided on their inner face, on surface 14. This embodiment of the fixation means allows an extremely accurate setting of the tightening, contrary to the buckles with a tongue, and the fixation rivet 15 permits the rotation of buckle 16 when the two half-shells are slightly offset.

On the other hand there is fixed in gutter 10, for example by means of rivets 17, a rigid bar 18, preferably of metal, maintaining the rigidity of the various elements and providing the holding in position of the inflatable lumbar pad 19. As shown in FIG. 4, said inflatable pad has the shape of a violin. It is made of a thermoplastic film or similar, and is subdivided by welding seams 20 into channels in a substantially vertical direction with sections decreasing from the center to the periphery. A valve 21 allows inflating the pad and setting its volume as a function of the variations in weight of the patient and of the evolution of the treatment while providing a lumbar compression.

The orthopaedic lumbo-sacral corset thus made allows providing a real elongation of the rachis due to the three elongation points formed by the abdominal compression at 6, the sub-costal support at 3 and the lumbar compression provided by the inflatable pad 19.

We claim:

1. An orthopaedic lumbo-sacral corset made of the assembly of semi-rigid elements and an inflatable pad comprising two side half-shells of a semi-rigid plastic material, connected along the adjacent dorsal edges by a semi-rigid thin band forming a hinge adapted to be generally aligned with the spine of the wearer, with attachment and tightening means between the adjacent front edges of the two half-shells and an inflatable lumber pad formed by two pads symmetric relative to and adjacent the hinge.

2. An orthopaedic lumbo-sacral corset according to claim 1, wherein the semi-rigid thin band forming the bridge is applied on the rear outer surface of the two half-shells the edges of which are spread apart so as to provide a space for the spinous processes.

3. An orthopaedic lumbo-sacral corset according to claim 1, wherein the inflatable lumbar pad has the shape of a violin, with an enlarged inferior lobe.

4. An orthopaedic lumbo-sacral corset according to claim 3, wherein the lumbar pad is subdivided into cavities and channels generally aligned with the spine of the wearer, the section of which is decreasing with radial distance from the hinge.

5. An orthopaedic lumbo-sacral corset according to claim 1, wherein the lumbar pad is associated with a rigid bar said bar being rigidly connected to the semi-rigid thin band forming a hinge opposite the said space provided for the spinous processes.

6. An orthopaedic lumbo-sacral corset according to claim 1, wherein each half-shell is formed with a side opening comprising elliptically contoured front and bottom edges adapted to conform to the wearer's iliac crest.

7. An orthopaedic lumbo-sacral corset according to claim 1, wherein each half-shell comprises a concave waist portion to be engaged between the iliac crest and the side sub-costal region, and a concave abdominal anterior surface.

8. An orthopaedic lumbo-sacral corset according to claim 1, wherein the attachment and tightening means between the adjacent front edges of the two half-shells are made of straps fixed in the vicinity of the anterior edge of one of the half-shells and rings attached in opposition to said straps adjacent the anterior edge of the other half-shell.

* * * * *

UNITED STATES PATENT AND TRADEMARK OFFICE
CERTIFICATE OF CORRECTION

PATENT NO. : 4,559,933
DATED : December 24, 1985
INVENTOR(S) : Denis BATARD et al.

It is certified that error appears in the above—identified patent and that said Letters Patent is hereby corrected as shown below:

Column 4, line 12, change "ber" to --bar--.

Signed and Sealed this

Twenty-ninth Day of April 1986

[SEAL]

Attest:

DONALD J. QUIGG

Attesting Officer

Commissioner of Patents and Trademarks